United States Patent [19]

Friese et al.

[11] Patent Number: 5,142,266
[45] Date of Patent: Aug. 25, 1992

[54] NTC TEMPERATURE SENSOR AND PROCESS FOR PRODUCING NTC TEMPERATURE SENSING ELEMENTS

[75] Inventors: Karl-Hermann Friese, Leonberg; Günther Stecher, Ludwigsburg; Hans-Martin Wiedenmann, Stuttgart, all of Fed. Rep. of Germany

[73] Assignee: Robert Bosch GmbH, Stuttgart, Fed. Rep. of Germany

[21] Appl. No.: 466,286

[22] PCT Filed: Aug. 30, 1988

[86] PCT No.: PCT/DE88/00528
§ 371 Date: Mar. 26, 1990
§ 102(e) Date: Mar. 26, 1990

[87] PCT Pub. No.: WO89/03115
PCT Pub. Date: Apr. 6, 1989

[30] Foreign Application Priority Data
Oct. 1, 1987 [DE] Fed. Rep. of Germany ....... 3733193

[51] Int. Cl.⁵ ............................................. H01C 7/10
[52] U.S. Cl. .................................. 338/22 R; 338/25; 338/28; 338/4
[58] Field of Search ............. 338/22 R, 225 D, 25, 338/28, 34; 374/144; 123/357, 381, 41.31

[56] References Cited
U.S. PATENT DOCUMENTS

| | | | |
|---|---|---|---|
| 3,952,276 | 4/1976 | Walch et al. | 338/28 |
| 4,314,145 | 2/1982 | Horsma | 338/22 R X |
| 4,526,481 | 7/1985 | Hansen | 374/144 |
| 4,586,829 | 5/1986 | Hübner et al. | 374/144 |
| 4,869,218 | 9/1989 | Fehlmann et al. | 123/357 |

*Primary Examiner*—Marvin M. Lateef
*Attorney, Agent, or Firm*—Michael J. Striker

[57] ABSTRACT

The NTC temperature sensor includes a NTC temperature sensing element having an NTC resistor and made of a laminated composite of ceramic films, which is so designed that the ambient air or oxygen supplied by electrolytic pumping has free access, via a channel in the laminated composite, to the NTC resistor. The NTC resistor is hermetically sealed from a gas being measured. Solid electrolyte films which conduct $O^{-2}$ ions, and films based on $Al_2O_3$ can be used to make the laminated composite. The NTC resistor characteristic curve is independent of the composition of the gas being measured. The laminated composite can be formed of at least three solid electrolyte ceramic films including a base film provided with punched-out interconnection holes and conductor tracks printed by thick film technology, an intermediate film having a punched-out channel and a channel enlargement around the ends of the conductor tracks forming the electrodes of the NTC resistor, and a covering film.

10 Claims, 5 Drawing Sheets

NTC TEMPERATURE SENSOR AND PROCESS FOR PRODUCING NTC TEMPERATURE SENSING ELEMENTS

BACKGROUND OF THE INVENTION

The invention relates to an NTC temperature sensor, particularly for use in the exhaust gas system of internal combustion engines, and also a process for producing NTC temperature sensing elements for the NTC temperature sensor.

It is generally known to use NTC temperature sensors having a temperature sensing element disposed in a housing to measure comparatively high temperatures such as prevail, for example, in the exhaust gases of internal combustion engines. Electron-conducting shaped oxide bodies and also, in particular, ion-conducting solid electrolyte shaped bodies, the latter based on oxides of tetravalent metals such as, in particular, $ZrO_2$, $CeO_2$, $HfO_2$ and $ThO_2$ having a certain content of divalent alkaline earth oxides and/or, preferably, trivalent oxides of the rare earths are suitable for producing the temperature sensing elements. Characteristic of such solid electrolytes is the fact that their electrical resistance decreases rapidly at temperatures from about 300° to 1200° C.

In the simplest manner, NTC temperature sensing elements have disc-type, pill-type or bead-type shaped resistance bodies having electrodes of a conductive material disposed on their sides situated opposite each other. To protect the shaped resistance bodies, it is furthermore known to house them in gas-tight housings or to coat them with a layer of glass. NTC temperature sensing elements of the type describe are known, for example, from German Auslegeschrift 2,429,866, German Patent Specifications 2,321,715 and 2,333,189 and also EP-A-0,056,752.

To determine the λ-value of gas mixtures, it is furthermore known to use planar exhaust gas sensors which can be produced in a particularly cheap manner by ceramic-foil and screen-printing technology. In this connection, reference is made, for example, to EP-A-0,188,900 and 0,142,993 and also German Offenlegungsschrift 3,017,947 and 3,543,759.

Disadvantages of the known sensing elements mentioned above is the fact that they age too rapidly during use, that their response times are too long and that their method of production is too expensive and/or their dimensions are too large. A particular disadvantage is the dependence of the characteristic curves of the resistance of such NTC materials on the composition of the gas, in particular in reducing gases or gas mixtures which can bring about oxygen deficiencies in the oxidic NTC resistance materials and thus alter their resistance values. The unavoidable diffusion of oxygen through highly refractory metal housings or through glass envelopes, in particular, causes undesirable changes in the resistance values.

ADVANTAGES OF THE INVENTION

The temperature sensor according to the invention having the sensing element formed by a composite of ceramic films which is encapsulated hermetically with respect to the gas being measured and is provided with a channel for admitting ambient air has the advantage over the known NTC temperature sensors that the temperature sensing element is not subject to any ageing due to the influence of varying $O_2$ partial pressures while being cheap to manufacture, has a high resistance to ageing of the resistance characteristic in rich and lean gas mixtures, for example in motor vehicle exhaust gases at 300°-1000° C. and has a construction free from extraneous potentials, is characterized by short response times owing to its low heat capacity, and is suitable for incorporation in very narrow housings as a consequence of its small dimensions.

A temperature sensing element suitable for an NTC temperature sensor according to the invention can be produced by known laminating technology from comparatively thin ceramic films having a thickness of, in particular, 0.1 to 0.6 mm, preferably of 0.25 to 0.3 mm which have previously been coated by known thick-film technologies with conductor tracks and, provided the films are not composed of a solid electrolyte which conducts oxygen ions, optionally with thermally stable NTC resistors. At the same time, the NTC resistors may be composed of materials such as are known, for example, from the book by E. D. Macklen entitled "Thermistors" published by Electrochemical Publications Ltd., 1979, pages 138-146.

Various types of NTC temperature sensors can be produced, depending on the choice of the films used for producing a sensing element for an NTC temperature sensor according to the invention. Preferred NTC temperature sensors which will be described in more detail below can be roughly subdivided into those having NTC sensor elements made of:

(A) ceramic films based on a solid electrolyte and
(B) ceramic films based on an insulator ceramic, in particular, based on $Al_2O_3$.

a combination of both film types also being optionally possible. In case (A), a part of the solid electrolyte substrate itself is utilized as NTC resistor, whereas in case (B), a laminar NTC resistor has to be deposited, for example, by screen-printing technology. Finally, the different type of oxygen supply to the NTC resistor makes it possible to produce further different types of NTC temperature sensors according to the invention. Thus, oxygen can be supplied to the NTC resistor in an advantageous manner by (a) a channel which may be produced by punching out or by using a cavity-forming agent and which may optionally contain a filling of porous material, and/or
(b) if ceramic films based on a solid electrolyte are used, by providing an oxygen reservoir due to a system of pump electrodes.

(A) Temperature Sensing Elements Made of Ceramic Films Based on a Solid Electrolyte Suitable films are known for producing this type of sensing element. Typically, such films may consist of about 50 to 97 mol-% of $ZrO_2$, $CeO_2$, $HfO_2$ or $ThO_2$ and 50 to 3 mol-% of CaO, MgO or SrO and/or $La_2O_3$, $Sc_2O_3$, $Gd_2O_3$, $Nd_2O_3$ and, in particular, $Y_2O_3$. Films made of yttrium-stabilized $ZrO_2$, so-called YSZ films, can be used in a particularly advantageous manner.

The NTC resistor is laid down by depositing 2 electrodes of defined dimensions on one of the films. The electrodes must be porous and must have as long a three-phase boundary as possible between solid electrolyte, electrode and gaseous oxygen. Such electrodes can be realized in a known manner from Pt-cermet electrodes having a supporting structure, for example made of YSZ particles, which conducts oxygen ions.

If films of this type are used, it is furthermore advantageous to dispose an insulating layer between the conductor tracks and the film surface. In an advantageous manner, as will be demonstrated later, such an insulating layer may be composed of a ceramic $Al_2O_3$ layer. In conjunction with ceramic films based on YSZ, it is advantageous to use porous $Al_2O_3$ layers with a view to matching the thermal expansion.

In accordance with a particular advantageous development of the invention, such an insulating layer between the conductor tracks and the solid electrolyte substrate may, however, also be produced by incorporating pentavalent metal ions such as, for example, $Nb^{5+}$ and $Ta^{5+}$ ions in the host lattice. The formation of such an insulating intermediate layer can be achieved by adding one or more compounds containing a pentavalent cation or one of higher valency to the suspension or paste used to form the conductor tracks and by allowing them to diffuse into the solid electrolyte substrate during the sintering process at temperatures of up to 1600° C., preferably 1350° to 1500° C., subsequent to the lamination process. Such insulating intermediate layers may also be produced in a corresponding manner in the interconnection holes.

To produce the conductor tracks, compounds which produce normal conductor tracks by normal thick-film technology may be deposited on the insulating layers and also the part of the solid electrolyte film which forms the NTC resistor with the conductor tracks. In an advantageous manner, use may be made, for example, of pastes based on noble metals, in particular based on platinum, or based on noble metal and cermet, in particular platinum and cermet. These pastes may be produced in a known manner using organic binders and/or adhesion promoters, plasticizers and organic solvents. If insulating intermediate layers are to be produced, small quantities of compounds containing a pentavalent cation or a cation of higher valency, for example $Nb_2O_5$, may be added to the paste. Suitable adhesion-promoting additives are, for example, $Al_2O_3$, $ZrO_2$ and silicates.

Interconnection holes can be produced by simply punching them out. The interconnection holes can be insulated, for example, by means of an insulating $Al_2O_3$ layer or by using a paste of the type described containing a pentavalent cation or cation of higher valency.

If ambient air or oxygen supplied by electrolytic pumping is to be fed via a channel in the laminated composite to supply the NTC resistor with oxygen, said channel may be produced in various ways. One possibility is to laminate the film having the printed-on conductor tracks and interconnection holes together with a further second solid electrolyte ceramic film out of which an air channel, which is advantageously enlarged in the region of the conductor tracks forming the electrodes, is punched before lamination, with the result that a free access of atmospheric oxygen to the electrodes of the NTC resistor is guaranteed. The hermetic sealing of the NTC resistor can be achieved in a simple manner, for example, by using a third solid electrolyte ceramic film with which the film having the punched-out channel is covered.

The channel may, however, also be produced in another way. Thus, it is also possible, in an advantageous manner, to produce the channel and optionally a channel enlargement by using a cavity forming agent. Suitable cavity forming agents are, for example, substances which can be ignited, decomposed or evaporated under sintering conditions, for example plastics, for example based on polyurethane, and salts, for example ammonium carbonate, and also thermal soot powder which burns out on sintering in an oxidizing atmosphere.

Optionally, further layers may participate in the construction of the laminated composite, for example adhesion-promoting layers and sealing layers. Individual films in the film composite may also be printed, in an advantageous manner, with sealing frames, for example composed of $ZrO_2$ paste.

The individual films can be laminated together in an advantageous manner with interlaminar binders, for example based on YSZ.

The laminated composite is subsequently sintered, for example by heating for 1 to 10 hours at temperatures of 1350° to 1500° C. After, but optionally even before, carrying out the sintering process, electrical contact areas may be printed on the outer side of the film in the area of the interconnection holes.

An oxygen reservoir due to a system of pump electrodes can be provided in an advantageous manner by laminating a second film made of solid electrolyte ceramic, which has previously been printed on both sides with pump electrodes and associated conductor tracks, onto a first film with printed-on conductor tracks to produce a cavity above the NTC resistor. The conductor tracks of said pump electrodes may be connected, for example, to a battery having a constant working voltage in the region of 0.5 to 1.0 volts. The areal extension of the pump electrodes may be small. The pump electrodes are preferably composed of a metal of the platinum group or of alloys of metals of the platinum group with other metals. They are preferably porous. The conductor tracks associated with the pump electrodes are preferably composed of the same material as the pump electrodes. The outer pump electrode may be covered with a porous ceramic film or also with another porous layer, for example based on magnesium spinel.

(B) Temperature Sensing Elements Made of Ceramic Films Bon an Insulator Ceramic

Temperature sensing elements of this type differ from the temperature sensing elements based on a solid electrolyte in principle in that it is necessary to print not only conductor tracks on one of the films used to produce the laminated composite, but also an NTC resistor and in that it is possible to dispense with the provision of insulating layers between film and conductor tracks and in the interconnection holes. Owing to their high thermal conductivity compared with $ZrO_2$ ceramic, a particularly advantageous type of ceramic film based on an insulator ceramic are those based on $Al_2O_3$ whose use in producing temperature sensors according to the invention is described, for example, below.

To produce the NTC resistor, it is possible to use pastes and suspensions which form a solid electrolyte and which contain the starting substances required to produce solid electrolytes of the type described and can be converted into ion-conducting solid electrolytes by a sintering process. Typically, powders based on zirconium dioxide stabilized with yttrium, for example $ZrO_2$ powder containing 5 to 15 mol-% of $Y_2O_3$, can consequently be used to produce the pastes and suspensions. Electron-conducting NTC resistor materials such as, for example, powders based on praseodymium oxide, in particular those composed of mixtures of praseodymium oxide and another metal oxide such as are known, for example, from German Patent Specification 2,333,189 and J.Am.Ceram.Soc. 61, No. 7-8, July-August 1978, page 318 et seq., are, however, also suitable. This means that, for example, powders based on Pr-Fe oxide or $Fe_2O_3(MnO)$ can also be used. In a similar manner, $Cr_2O_3/Al_2O_3$ NTC resistor layers such as are described, for example, in EP-A-056,752 can be used.

Taking account of the need to print an NTC resistor and dispensing with the provision of insulating films, the production of an NTC temperature sensing element made of ceramic films based on $Al_2O_3$ can consequently be carried out in the manner described for NTC temperature sensors made of ceramic films based on a solid electrolyte. Accordingly, in the case of ceramic films based on $Al_2O_3$, the supply of oxygen to the NTC resistor can consequently also take place via a channel open to the ambient air or one filled with porous material.

Porous materials and substances are in this case understood to mean those which prevent, or at least effectively impede, the penetration of contaminants such as, for example, oil vapours, vapours from plastic components and substances with a reducing action and nevertheless make possible an adequate supply of oxygen to the NTC resistor. In this connection a channel filled with a porous material or substance can be produced in various ways, in particular by using substances which do not sinter compactly at the sintering temperature used, and pore forming agents such as, for example, theobromine or thermal soot or other substances which can be ignited, evaporated or decomposed during the sintering process and which form continuous pore channels. Suitable substances which do not sinter compactly at the sintering temperature used are, for example, coarse-grained $ZrO_2$, Mg spinel or $Al_2O_3$ with grain size of up to 10 μm.

SUMMARY OF THE INVENTION

In the simplest manner, an NTC temperature sensing element according to the invention can be produced from ceramic films based on $Al_2O_3$, for example, by punching interconnection holes out of a first film, then printing electrical contact areas and conductor tracks and also, finally, an NTC resistor onto the film and laminating onto said film, preferably using an interlaminar binder based on $Al_2O_3$, a further ceramic film based on $Al_2O_3$ to form a cavity over the NTC resistor. In this connection, the cavity can be produced in various ways, for example, by using a cavity forming agent of the type already described which evaporates, ignites or decomposes at the sintering temperature of the laminated composite, or by using a further interposed film out of which an air supply channel has previously been punched.

According to an advantageous development of the invention, mixtures of a cavity forming agent and a material which fails to sinter compactly at the sintering temperature of the laminated composite, for example mixtures of a cavity forming agent and particles of $ZrO_2$, Mg spinel or $Al_2O_3$ are used instead of a cavity forming agent. In this manner, a porous filling of the air space gap is produced which prevents the gap cover from sinking as a result of plastic deformation during the sintering process and consequently prevents the gap from closing.

The sintering is carried out in an advantageous manner by heating for several hours, for example 3 hours, at a temperature of up to 1600° C. Adding suitable fluxes, preferably based on silicate in an adequate amount, may also reduce the maximum sintering temperature to be used. This applies in a similar manner to the use of $Al_2O_3$ raw materials with high sintering activity.

The electrical contact areas may be printed on even after carrying out the sintering process and sintered in a further sintering process at comparatively low temperatures. In this case, cheap and low-resistance contact materials, for example based on Ag, may be used.

The NTC temperature sensing elements described can be inserted in housings of known construction and designs, for example in those of the type known from German Offenlegungsschrift 3,206,903.

BRIEF DESCRIPTION OF THE DRAWING

The accompanying drawing serve to explain the invention more precisely. In detail.

DESCRIPTION OF THE PREFERRED EMBODIMENTS

Figure 1:
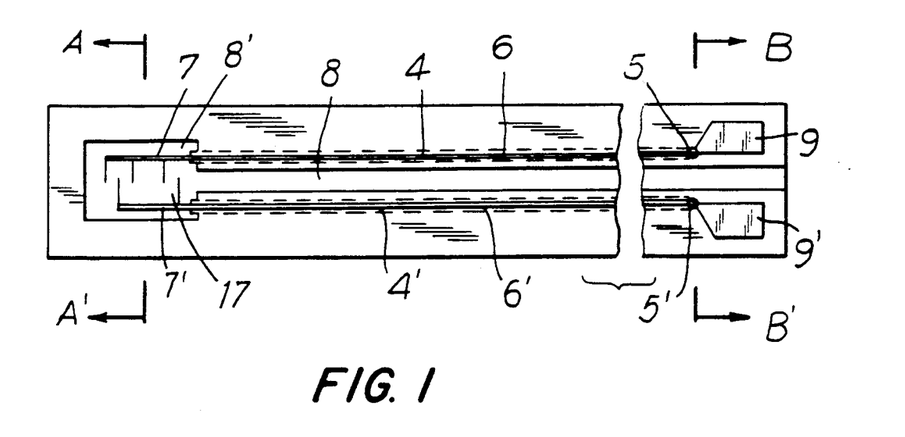
FIG. 1 shows diagrammatically a plan view of an NTC temperature sensing element according to the invention comprising solid electrolyte films with punched-out channel for supplying ambient air, in which element the NTC resistor is formed by one of the films.
Figure 1A:
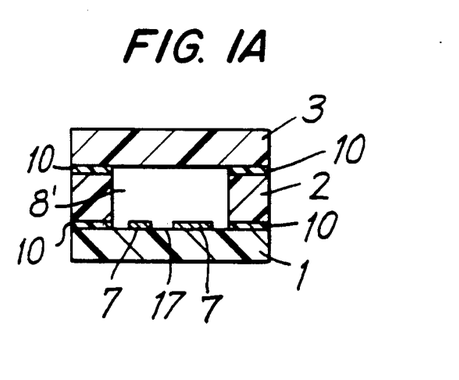
FIG. 1A shows diagrammatically a section along A—A' of FIG. 1.
Figure 1B:
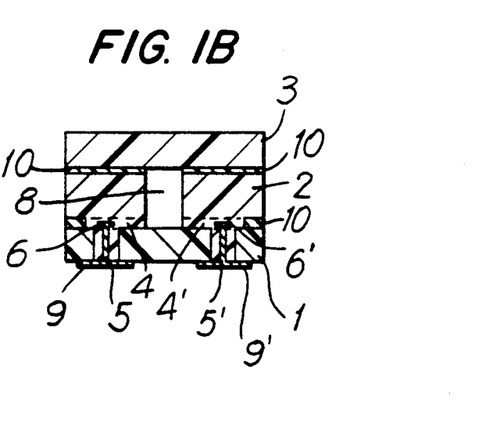
FIG. 1B shows diagrammatically a section along B—B' of FIG. 1.

The embodiment shown diagrammatically in FIGS. 1, 1A and 1B of an NTC temperature sensing element according to the invention comprises essentially three solid electrolyte films 1, 2 and 3, for example films based on stabilized zirconium dioxide, of which the base film 1 has punched-out interconnection holes 5 and 5' and the center film 2 has a punched-out air channel 8 having the enlargement 8', and the film 3 covers the air channel 8 with the enlargement 8, from above in conjunction with the two films 1 and 2. Provided between the conductor tracks 6 and 6', for example Pt conductor tracks, and the films 1 and 2 are insulating layers or insulating regions 4 and 4'. The electrodes 7 and 7' are formed by the ends of the conductor tracks 6 and 6'. In the case of the exemplary embodiment shown, they are of mutually interdigitated construction in order to reduce the resistance. The film 1 with the electrodes 7 and 7' forms the NTC resistor 17. The other end of the conductor tracks 6 and 6' is connected to electrical contact areas 9 and 9' respectively via interconnections 5 and 5'. As indicated by 10, the three films are laminated together by means of a binder. The binder may be composed, for example, of a normal interlaminar binder based on zirconium dioxide stabilized with yttrium oxide and may assume the function of the sealing frame for the air channel. The NTC temperature sensing element of FIGS. 1, 1A and 1B is installed in a pipe 41 containing the gas to be measured 43, preferably the exhaust gas of an internal combustion engine, in such a way that the NTC resistor 17 is hermetically sealed from the gas being measured 43. Of course, the embodiment of the sensing element of Figure contains a channel 8, which is open to the atmosphere in the surroundings S on the outside of the pipe 41 and the gas being measured, e.g. the exhaust gas, is dissiptated into the atmosphere. Air can flow from the surroundings S into the sensing element as indicated by the arrow 45. Nevertheless, the sensing element is open only to the atmosphere, which contains a fixed proportion of oxygen, because the exhaust gas is dissipated into the atmoshphere.

Figure 2:
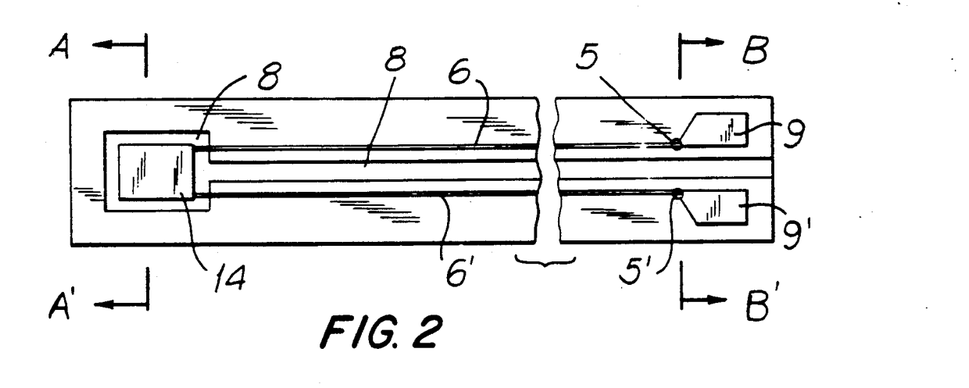
FIG. 2 shows diagrammatically a plan view of a further embodiment of a temperature sensing element according to the invention comprising three ceramic films based on $Al_2O_3$ with punched-out channel for supplying ambient air and with a printed NTC resistor.
Figure 2A:
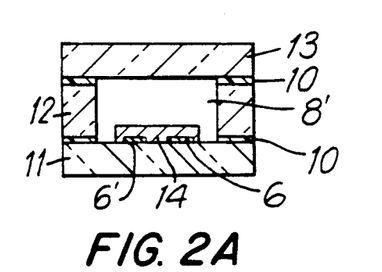
FIG. 2A shows a section along A—A' of FIG. 2.
Figure 2B:
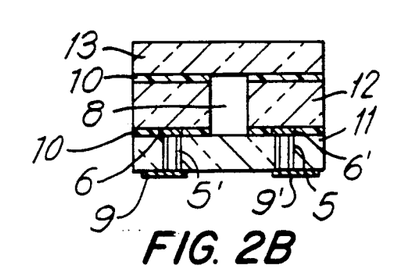
FIG. 2B shows diagrammatically a section along B—B' of FIG. 2.

The embodiment of an NTC temperature sensing element according to the invention shown diagrammatically in FIGS. 2, 2A and 2B differs from the embodiment shown in FIGS. 1, 1A and 1B essentially in that this time the NTC resistor is not formed, as in the case of the embodiment shown in FIGS. 1, 1A and 1B, with the participation of the film 1, but by a printed resistor layer 14. In the case of the embodiment shown in FIGS. 2, 2A and 2B, the films 11, 12 and 13 are composed of films based on an insulator ceramic, for example based on $Al_2O_3$. Accordingly, a special insulating layer between the conductor tracks 6 and 6, and the films 11 and 12 is not necessary either. The printed resistor layer 14 may be, for example, a layer based on zirconium dioxide stabilized with yttrium containing, for example, 10 mol-% of yttrium oxide. The NTC temperature sensing element of FIGS. 2, 2A and 2B is installed in a pipe 41 containing the gas to be measured 43, preferably the exhaust gas of an internal combustion engine, in such a way that the NTC resistor 17 is hermetically sealed from the gas being measured 43.

Figure 3:
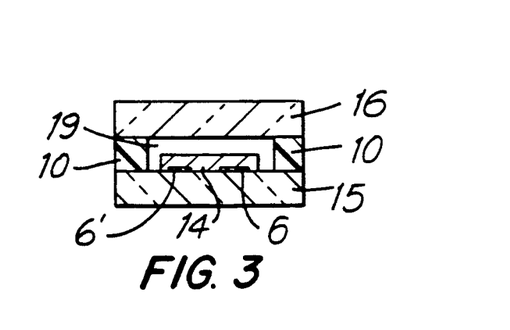
FIG. 3 shows diagrammatically a section through a further embodiment of a NTC of a temperature sensing element according to the invention comprising two films based on $Al_2O_3$ with oxygen supplied through a tunnel which has been produced by thick-film technology.

FIG. 3 shows an embodiment of an NTC temperature sensing element according to the invention in section, which element is formed from only two films 15 and 16 based on $Al_2O_3$. The films 15 and 16 are laminated together by means of a binder 10 and form a tunnel 19 which is produced by screen-printing technology using substances of the specified type which can be burnt out, evaporated or decomposed and which may optionally be filled with a porous material, via which tunnel air is supplied.

Figure 4:
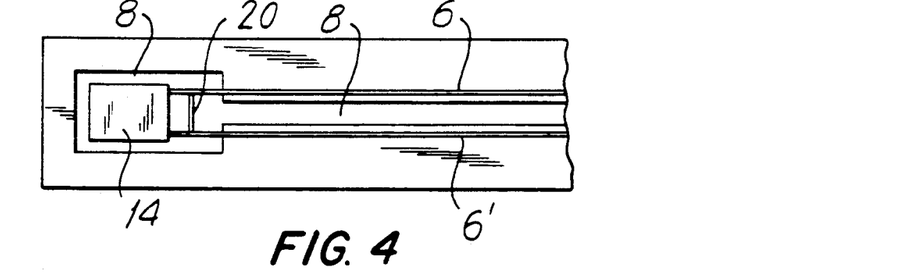
FIG. 4 shows diagrammatically a plan view of the arrangement of an additional monitoring resistor.

FIG. 4 illustrates the arrangement of an additional monitoring resistor 20 between the conductor tracks 6 and 6' in the air channel enlargement 8' of an NTC temperature sensing element according to the invention, for example of the type shown in FIG. 2. Such a monitoring resistor having PTC characteristics is used, in particular, to check the serviceability of the NTC sensor at low application temperatures, for example room temperature. In an advantageous manner, this resistor may be a platinum-cermet resistor of, for example, 10 k$\Omega$.

Figure 5:
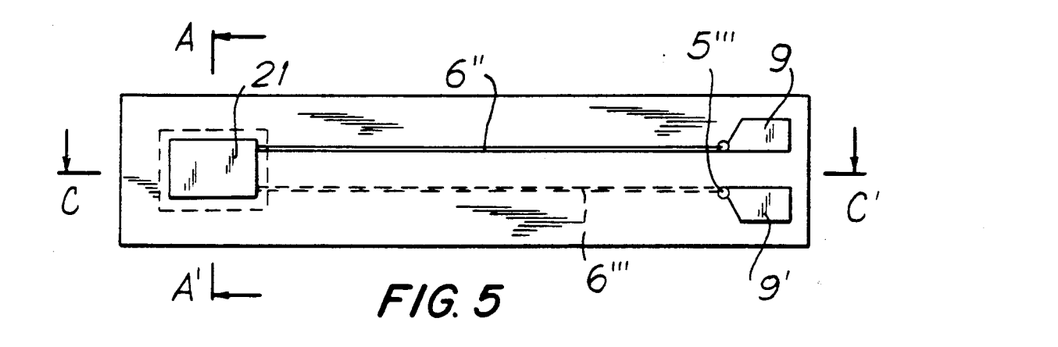
FIG. 5 shows diagrammatically a plan view of a further embodiment of a NTC temperature sensing element according to the invention in which an oxygen reservoir is maintained by providing pump electrodes.

The embodiment shown in FIG. 5 of an NTC temperature sensing element according to the invention composed of three films 1, 2 and 3 based on YSZ does not have a channel open to the ambient air. In this embodiment, an oxygen reservoir is maintained by providing pump electrodes 21 and 22, for example platinum electrodes. The pump electrodes are connected to a battery, which is not shown, via the conductor tracks 6" and 6"'. Interconnections 5 or 5' are provided for the NTC resistor 17 and the conductor tracks 6, 6' and the interconnection 5"' for the conductor track 6"'.

Figure 6:
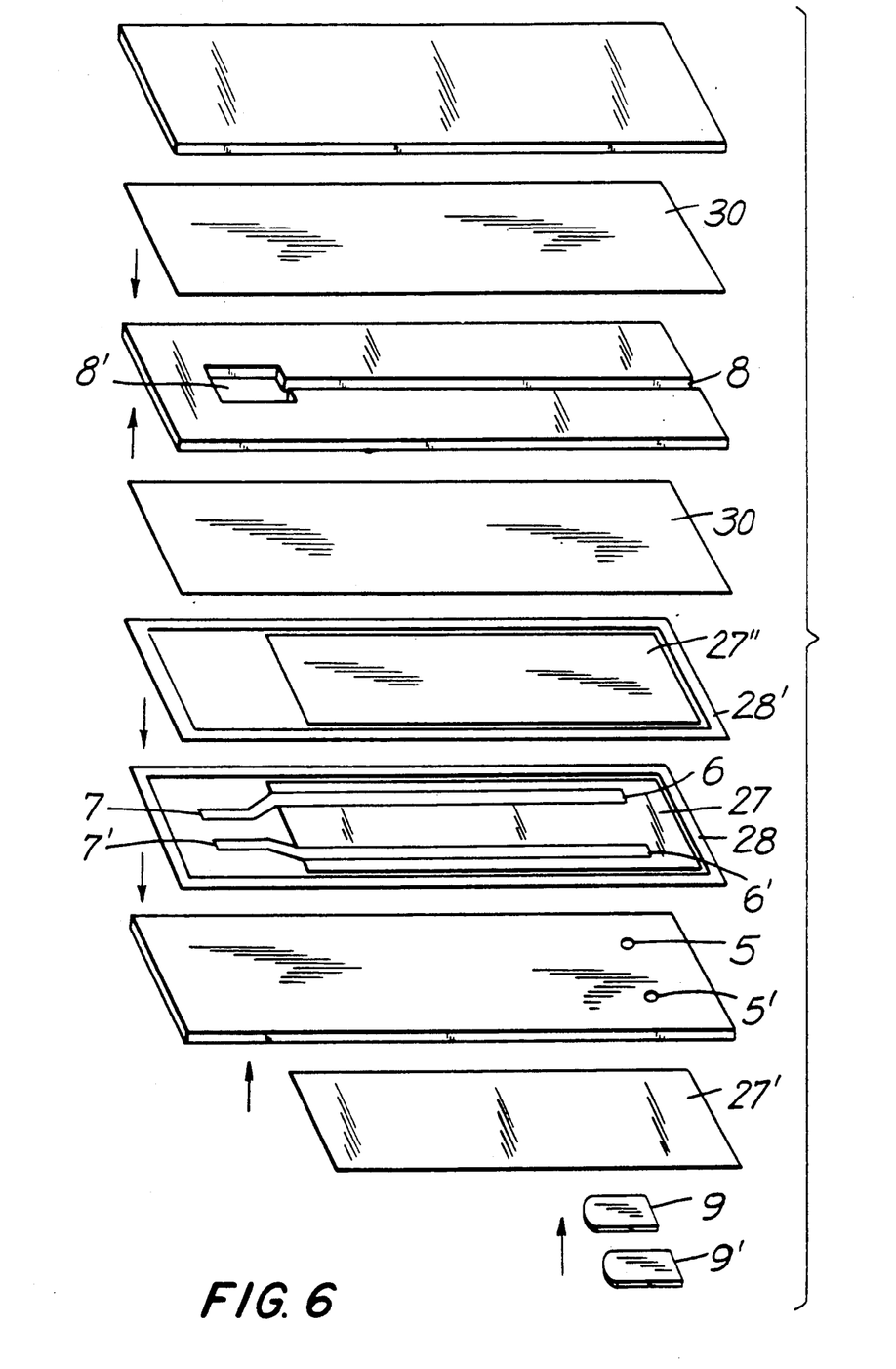
FIG. 6 shows diagrammatically the individual process steps in producing an advantageous embodiment of an NTC temperature sensing element according to the invention and corresponding to FIG. 1, having three films.

FIG. 6 illustrates diagrammatically the stepwise production of an advantageous embodiment of an NTC temperature sensing element according to the invention starting from three solid electrolyte ceramic films 1, 2, 3. According to this, the procedure is advantageously adopted that 1. an insulating layer 27 is printed on a solid electrolyte ceramic film 1 at least in the region of the conductor tracks to be printed and a similar film 27' is printed on the rear side of the film, the latter serving to suppress the sintering process and also to insulate the connecting contacts, 2. interconnection holes 5, 5' are punched in the solid electrolyte ceramic film 1, 3. an insulating layer is produced in the interconnection holes 5, 5' and an electrical conductor is deposited on the insulating layer, 4. connecting contacts 9, 9' are printed on the rear side of the film 1 in the region of the insulating layer 27', 5. conductor tracks 6, 6' are printed on the front side of the solid electrolyte ceramic film 1 in the region of the insulating layer 27 and also electrodes 7, 7' in non-insulated regions, and finally a hermetically sealing frame 28 is printed, 6. on the printed side of the film 1, the conductor tracks 6, 6' are insulated by printing on an insulating layer 27" and the hermetically sealing frame is reinforced by printing on the layer 28' in order to achieve an approximately equal layer thickness for all the layers, 7. a second film 2 is coated on both sides with an interlaminar binder 30, for example based on YSZ, and an air channel 8 with an enlargement 8' is punched in the coated film 2, 8. the film 2 is mounted on the film 1, 9. a further solid electrolyte ceramic film 3 printed with an interlaminar binder 30 is mounted on the film 2 as a covering film, 10. the solid electrolyte ceramic films 1, 2 and 3 are laminated together, and 11. the film composite is sintered at a temperature of 1350° to 1500° C. for 1 to 10 hours.

Deviations from this procedure are possible. Thus, for example, the contact areas 9, 9' can be printed on after the sintering process and the insulating layer 27" can be printed, for example, onto the film 2.

Figure 7:
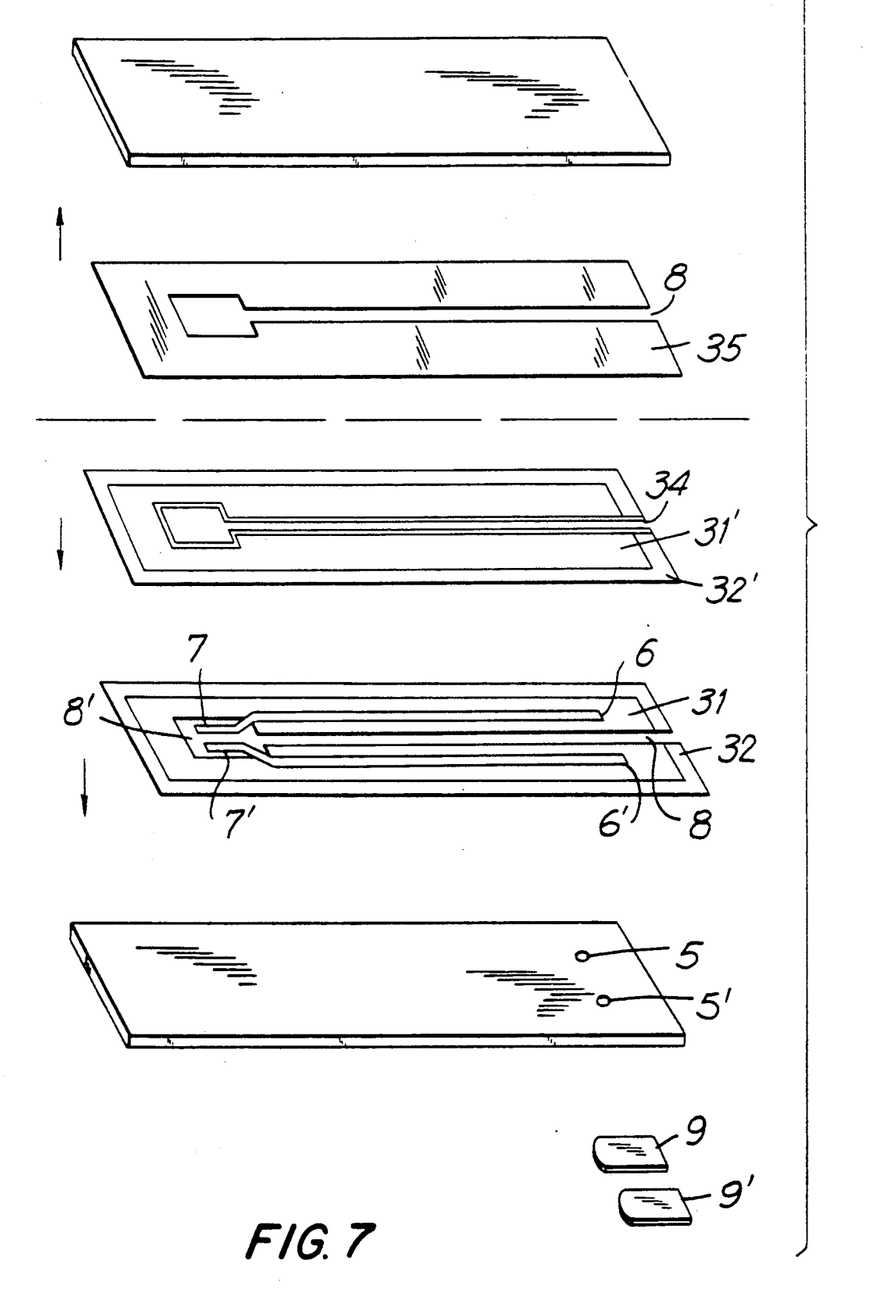
FIG. 7 shows diagrammatically the individual process steps in producing a second advantageous embodiment of an NTC temperature sensing element according to the invention having only two films and an air supply channel by screen-printing technology.

According to a second, particularly advantageous embodiment of the process according to the invention which is shown diagrammatically in FIG. 7, the procedure is adopted that 1. an insulating porous $Al_2O_3$ layer 31 with cut-outs 8, 8' is first printed on a solid electrolyte ceramic film 1,
2. interconnection holes 5, 5' are punched in the film and an electrical conductor is introduced,
3. electrodes 7, 7', conductor tracks 6, 6', a hermetic sealing frame 32 and also a second insulating layer 31' are printed on the film 1 and finally a layer 34 composed of a substance which can be burnt out or evaporated off is printed into the cut-outs 8, 8' and the hermetically sealing frame is reinforced with the layer 32',
4. contact areas 9, 9' are printed on,
5. a second solid electrolyte ceramic film 2 containing a binder layer 35, for example based on YSZ, with suitable cut-outs 8, 8, is deposited on the film 1 and the films are laminated together, and
6. the composite body is sintered.

In this embodiment, too, deviations from the procedure described are possible. For example, a mixture of a substance which can be burnt out or evaporated off and particles composed of $ZrO_2$, Mg spinel or $Al_2O_3$, which form an air channel with porous filling in the sintering process, can be printed into the cut-outs 8 and 8' in the process step 3.

According to a further particularly advantageous embodiment of the process according to the invention, the procedure is adopted that 1. a paste containing the components normally necessary for producing conductor tracks, for example, based on Pt-cermet or Pt-alloy-cermet having a content of $Nb_2O_5$ or another technically equivalent compound which supplies pentavalent cations or cations of higher valency for diffusion into the film substrate, and also electrodes are printed on a solid electrolyte ceramic film 1 for the purpose of producing conductor tracks,
2. interconnection holes are punched in the film 1,
3. the interconnection holes are insulated and an electrical conductor, for example of the type used for the conductor tracks, is deposited.
4. a second solid electrolyte ceramic film 2 with punched-out air channel and a channel enlargement is mounted on the printed side of the film 1 in a manner such that the electrodes are not covered by the film 2,
5. a further solid electrolyte ceramic film 3 is mounted on the film 2 as covering film,
6. contact areas are printed on the rear side of the film 1,
7. the films 1, 2 and 3 are laminated together and
8. the film composite is sintered at a temperature of 1350° to 1500° C. for 1 to 10 hours in a manner such that not only is a stable film composite obtained but also enough pentavalent cations or cations of higher valency are diffused into the film substrate to obtain insulating layers in the conductor regions of the films.

In the case of this embodiment, too, the individual films may be laminated together using an inter-laminar binder.

EXAMPLE 1

Production of a first embodiment according to the invention of an NTC temperature sensing element from ceramic films based on a solid electrolyte with punched-out channel for supplying ambient air.

To produce an NTC temperature sensing element according to the invention of the construction shown diagrammatically in FIGS. 1 to 1B, the following procedure, as illustrated diagrammatically in FIG. 6, was adopted:

Three ceramic films 1, 2 and 3 based on YSZ and having a thickness of 0.3 mm in each case (in the unsintered state) were used. In a first process stage, $Al_2O_3$ insulating layers 4 and 4' 15 to 20 μm thick were printed on the base film 1 in the conductor track regions, after which interconnection holes 5 and 5' having a diameter of 0.4 mm were punched out and provided with an $Al_2O_3$ insulating layer and also with an electrically conducting $Pt/Al_2O_3$ cermet layer thereon.

In a second process stage, conductor tracks 6, 6' made of Pt-cermet or Pt-alloy cermet and approximately 10–15 μm thick were printed on the base film 1. In the present case, the equally thick ends of the conductor tracks forming the electrodes 7, 7' were printed as raster to reduce the resistance.

An $Al_2O_3$ insulating layer with electrical contact areas 9 and 9' on top of it was printed on the rear side of the base film 1.

At the same time, after an interlaminar binder had previously been printed on both sides of the film, an air channel 8 with an enlargement 8' was punched out of the ceramic film 2. An $Al_2O_3$ insulating layer was printed on the regions which come into contact with the conductor tracks when film 2 is laminated together with film 1. Film 2 was then laminated together with the solid electrolyte film serving as covering film using an interlaminar binder. The interlaminar binder used to produce the NTC temperature sensor was composed of the same raw materials and had the same composition as the electrolyte films used.

After the composite body had been formed by mutual lamination, the body was sintered by heating for 4 hours at a temperature in the region of 1400° C.

The temperature sensing element was inserted in a housing of the type known from German Offenlegungsschrift 3,206,903 and used to measure the temperature of exhaust gases from internal combustion engines.

EXAMPLE 2

The procedure adopted was as in Example 1, with the distinction, however, that the provision of the $Al_2O_3$ insulating layer on the base film 1 and the insulation of the interconnection holes by means of an $Al_2O_3$ insulating layer were dispensed with. This time, in order to achieve an adequate insulation of the base film, a platinum-cermet paste of the following composition was used to produce the conductor tracks:

85 parts by weight of Pt powder,
12.5 parts by weight of $Nb_2O_5$ powder,
2.5 parts by weight of $Al_2O_3$ powder.

Pastes of the same composition were used to insulate the interconnection holes. However, it was also possible to successfully use, for example, a paste containing the following solid constitutents:

85 parts by weight of Pt powder,
15 parts by weight of niobium oxide $Nb_2O_5$.

The electrodes 7, 7' were printed with Pt-cermet paste without adding $Nb_2O_5$.

EXAMPLE 3

Production of an NTC temperature sensing element from ceramic films based on $Al_2O_3$ with a channel punched out for supplying ambient air.

An NTC temperature sensing element of the type shown diagrammatically in FIGS. 2 to 2B was produced starting from three ceramic films 11, 12, 13 based on $Al_2O_3$ each having a thickness of 0.3 mm. Conductor tracks 6 and 6' and also an NTC resistor 14 were first printed by thick-film technology on the base film 11. A Pt-cermet paste was used to produce the conductor tracks and a $ZrO_2$ paste stabilized with yttrium (10 mol-% $Y_2O_3$) for producing the NTC resistor 14. In a further process step, interconnection holes 5 and 5' were punched in the film 11. The interconnection holes were coated with a Pt-$Al_2O_3$ 1 paste Contact layers 9, 9', also based on Pt-$Al_2O_3$, were printed on the rear side of the film 11 over the interconnection holes. At the same time, an air channel 8 with an enlargement 8' was punched out of a further film 12 based on $Al_2O_3$ on both sides of which an interlaminar binder based on $Al_2O_3$ had been printed previously. This film 12 was then laminated together with a film based on $Al_2O_3$ serving as covering film 13 and with the base film 11.

The composite laminated together was then sintered by heating for 2 hours at temperatures in the region of 1600° C.

The temperature sensing element was inserted into a housing of the type known from German Offenlegungsschrift 3,206,903 and used to measure the temperature of exhaust gases from internal combustion engines.

EXAMPLE 4

Further NTC temperature sensing elements were produced as described in Example 3, but this time resistors based on $Cr_2O_3/Al_2O_3$ mixed oxide with a proportion of 22 % by weight of $Al_2O_3$ were used instead of the NTC resistor based on YSZ.

EXAMPLE 5

Further NTC temperature sensing elements were prepared as described in Example 3, but this time films with a content of a silicate flux based on alkaline earth oxide-silicate were used instead of the virtually pure $Al_2O_3$ films used in Example 3. The silicate content of the films was 5% by weight.

EXAMPLE 6

Production of a further embodiment of an NTC temperature sensing element according to the invention made of solid electrolyte films with an oxygen supply via a tunnel by thick film technology as shown diagrammatically in FIG. 7.

Two ceramic films 1 and 2 based on YSZ each with a thickness of 0.3 mm were used.

A porously sintering $Al_2O_3$ layer 31 having cutouts 8, 8' was first printed on the film 1. Subsequently, interconnection holes 5 and 5' were punched out which were provided with an $Al_2O_3$ insulating layer and an electrically conducting Pt/$Al_2O_3$-cermet layer. Platinum-cermet electrodes 7, 7' and conductor tracks 6, 6', and also a frame 32 made of YSZ binder compound were now printed on the film 1 after which a substance which could be burnt out or evaporated off, e.g. thermal soot or theobromine, was printed into the cut-outs 8, 8'. Finally, to insulate the conductor tracks, a second porously sintering $Al_2O_3$ layer 31' and then a further frame made of YSZ binder compound were printed on. Contact areas 9, 9' made of Pt/$Al_2O_3$-cermet paste were printed on the rear side of film 1 over the interconnecting holes. A binder layer 35 made of YSZ binder compound was printed on film 2, after which films 1 and 2 were laminated together. After the mutual lamination, the composite body obtained was sintered by heating for 4 hours at a temperature in the region of 1400° C., in which process the substance which could be burnt out or evaporated off was burnt out or evaporated off to form a channel.

The temperature sensing element produced was inserted in a housing of the type known from German Offenlegungsschrift 3,206,903 and used to measure the temperature of exhaust gases from internal combustion engines.

EXAMPLE 7

The process described in Example 7 was modified in the respect that, instead of the substance which ignites completely and forms a hollow tunnel, a mixture was used which was composed of (a) a completely combustible substance such as theobromine and (b) of a porously sintering material, i.e. material which fails to sinter compactly at the sintering temperature employed, i.e. of coarse-grained $ZrO_2$, Mg spinel or $Al_2O_3$ having a graing size of, for example, up to 10 $\mu$m. In this manner, the sintering process produced a filled tunnel which prevents the penetration of contaminants such as, for example, oil vapours, vapours from plastic components and other reducing substances which may jeopardize the stability of the NTC resistor.

EXAMPLE 8

A further NTC temperature sensor was prepared by the process described in Example 6, but this time an additional monitoring resistor 20 for low application temperatures based on Pt-cermet of approx. 10 k$\Omega$ was printed on the film 1 in the air channel 8 between the two conductor tracks 6 and 6' together with the latter.

EXAMPLE 9

Figure 5A:
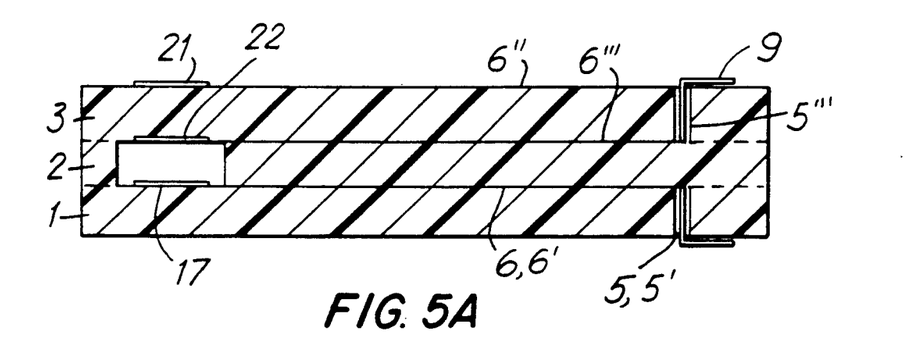
FIG. 5A shows diagrammatically a side view of the NTC temperature sensing element as a sectional view along C—C' of FIG. 5.
Figure 5B:
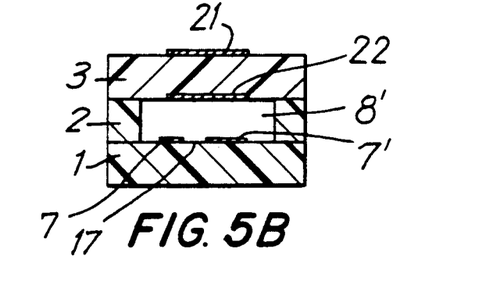
FIG. 5B shows diagrammatically a section along A—A' of FIG. 5.

To produce an NTC temperature sensing element of the type shown diagrammatically in FIGS. 5 to 5B, three films 1, 2 and 3 based on a solid electrolyte, for example based on YSZ, were used. After printing an $Al_2O_3$ insulating layer, which was cut out in the region of the electrodes, punching out interconnection holes 5, 5', insulating the same and depositing an electrical conductor, printing on connecting contracts 9, 9', conductor tracks 6, 6' and, to form an NTC resistor 17, electrodes 7, 7' were printed on the film 1.

After printing $Al_2O_3$ insulating layers on both sides which were cut out in the region of the pump electrodes, punching out an interconnecting hole 5''' for the conductor track 6''' of the internal pump electrode 22, insulating the same and depositing an electrical conductor, conductor tracks 6'' and 6''' and also pump electrodes 21 and 22 were printed on the film 3.

After mutual lamination of the films 1, 2 and 3 using an interlaminar binder, the composite body obtained was sintered.

In this manner, an NTC temperature sensing element was produced having a $O_2$ reservoir due to electrolytic pumping.

We claim:

1. NTC temperature sensor, in particular for measuring gas temperature of a gas in an exhaust gas system of an internal combustion engine, comprising a sensing element arranged in a housing, the sensing element including an NTC resistor and conductor tracks which connect electrically to the NTC resistor, the sensing element being formed from a laminated composite of a plurality of ceramic films, the laminated composite having a channel (8) for permitting free access of a member selected from the group consisting of ambient air and oxygen supplied electrolytically by pumping to the NTC resistor (14, 17), and means for hermetically sealing the NTC resistor with respect to the gas whose gas temperature is being measured.

2. NTC temperature sensor according to claim 1, wherein the laminated composite is formed from at least three solid electrolyte ceramic films including a base film provided with a plurality of punched-out interconnection holes (5, 5') and the conductor tracks (6, 6') printed on by a thick-film technology method, the conductor tracks (6, 6') having ends forming electrodes (7, 7') an intermediate film (2) having a punched-out channel (8) and a channel enlargement (8') in the vicinity of the ends of the conductor tracks (6, 6') forming the electrodes (7, 7') of the NTC resistor, and a covering film (3).

3. NTC temperature sensor according to claim 2, wherein the solid electrolyte ceramic films are composed of $ZrO_2$ stabilized with yttrium and wherein insulating layers (4, 4') are disposed between the conductor tracks (6, 6') and between the base film (1) and intermediate film (2).

4. NTC temperature sensor according to claim 1, wherein the ceramic films comprise $Al_2O_3$, and the composite laminate includes a base film (11) having a plurality of conductor tracks (6, 6') printed on a by a thick-film technology method and a printed on NTC resistor (14) connected electrically with the conductor tracks, and two additional films (12, 13) which are laminated together with a base film to form the channel(8, 8').

5. NTC temperature sensor according to claim 4, wherein the NTC resistor is composed of $ZrO_2$ stabilized with yttrium and containing about 3 to 15 mol-% of $Y_2O_3$.

6. NTC temperature sensor according to claim 4, wherein the sensing element has two conductor tracks, and further comprising an additional monitoring resistor (20) connected electrically between the two conductor tracks (6, 6').

7. NTC temperature sensor according to claim 1, wherein the laminated composite of the sensing element is formed from three ceramic films (1, 2, 3) laminated together and based on a solid electrolyte, said films form a channel (8') containing the NTC resistor (17), the channel being filled with a porous material, and further comprising at least two pump electrodes (21, 22), said pump electrodes being operable to maintain an oxygen reservoir in the channel (8') by electrolyte pumping.

8. NTC temperature sensor according to claim 1, further comprising an interlaminar binder, the ceramic films of the laminated composite being laminated together by the interlaminar binder.

9. NTC temperature sensor, in particular for measuring gas temperature of a gas in an exhaust gas system of an internal combustion engine, comprising a sensing element arranged in a housing, the sensing element including an NTC resistor and conductor tracks which connect electrically to the NTC resistor, the sensing element being formed from a laminated composite of a plurality of ceramic films, the laminated composite having a channel (8) for permitting free access of a member selected from the group consisting of ambient air and oxygen supplied electrolytically by pumping to the NTC resistor (14, 17), and means for maintaining an oxygen partial pressure over the NTC resistor substantially constant.

10. The NTC temperature sensor according to claim 9, wherein said means for maintaining the oxygen partial pressure include means for preventing contact of the NTC resistor with the gas being measured.

* * * * *